United States Patent [19]

Takano et al.

[11] Patent Number: 5,374,768
[45] Date of Patent: Dec. 20, 1994

[54] CYCLOHEXENE DERIVATIVES

[75] Inventors: Seiichi Takano; Kunio Ogasawara, both of Sendai, Japan

[73] Assignee: Chisso Corporation, Tokyo, Japan

[21] Appl. No.: 127,125

[22] Filed: Sep. 27, 1993

Related U.S. Application Data

[63] Continuation-in-part of Ser. No. 101,765, Aug. 4, 1993, abandoned.

[30] Foreign Application Priority Data

Aug. 19, 1992 [JP] Japan .................. 4-290684

[51] Int. Cl.⁵ .............................. C07C 67/02
[52] U.S. Cl. ...................... 560/256; 560/249
[58] Field of Search ............ 560/256, 249, 101, 116

[56] References Cited

U.S. PATENT DOCUMENTS

| | | | |
|---|---|---|---|
| 4,608,194 | 8/1986 | Boden et al. ............. | 560/256 X |
| 4,855,488 | 8/1989 | Gude et al. ............. | 560/256 X |
| 4,929,599 | 5/1990 | Giersch et al. ............. | 560/256 X |
| 4,959,349 | 9/1990 | Ohnuma et al. ............. | 560/256 X |
| 5,089,625 | 2/1992 | Sato et al. ............. | 548/110 |

*Primary Examiner*—Arthur C. Prescott
*Attorney, Agent, or Firm*—Wenderoth, Lind & Ponack

[57] ABSTRACT

The present invention provides a process for producing an optically active cyclohexenone derivative characterized in that it comprises using a specialized cyclohexene derivative as a starting material, reacting the derivative with lipase by regioselective transesterification to obtain optically active cyclohexenone derivatives, represented by the following formulae.

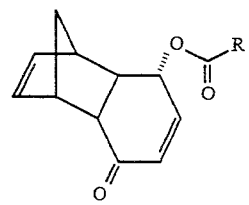

(2)

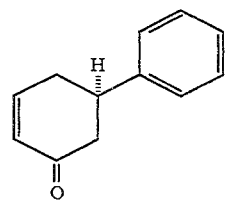

(7)

8 Claims, No Drawings

CYCLOHEXENE DERIVATIVES

This application is a continuation-in-part of application Ser. No. 08/101,765, filed Aug. 4, 1993, now abandoned.

BACKGROUND OF THE INVENTION

The present invention relates to optically active cyclohexene derivatives, a process of production of optically active cyclohexenone derivatives, which are represented by the following formulae, useful as a starting material for synthesizing natural products, and intermediates used for the above production.

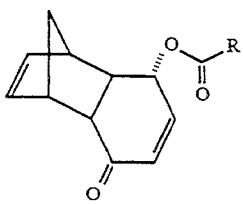

(2)

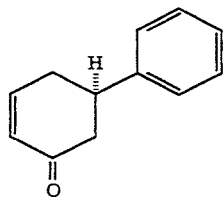

(7)

The optically active cyclohexenone derivative represented by the formula (7) is a very useful compound as an intermediate for synthesizing natural materials (for example, "Total Synthesis of Natural Products", ApSimon edit, vol. 2, 1973 and vol. 5, 1983, and J. d'Angelo, Tetrahedron, 32, 2979 (1976)). Takei et al. synthesized an optically active cyclohexenone derivative (7) by using optically active 5-trimethylsilylcyclohexene-2-one as a starting material (J. Chem. Soc., Chem. Commun., 1988, 430).

However, optically active 5-trimethylsilylcyclohexene-2-one is obtained by repeated recrystallization of a diastereomer salt synthesized from a racemate of the starting material with cinchonidine and toluenethiol. The method is not for practical use because of many steps and low yield of 3% (Tetrahedron, Lett., 28, 5669 (1987)).

The optically active cyclohexenone derivative represented by the formula (2) is a starting material for synthesizing eutypoxide B, a metabolite of the fungus *Eurypa lata*. The racemic total synthesis of eutypoxide B has been reported by Tabacchi and co-workers by employing the Diels-Alder reaction as the key step (Helv. Chim. Acta, 75, 276 (1992)). However, the key reaction directed diasterofacial selection in a wrong way to furnish the diastereomeric mixture containing the desired epimer only in ratio of one which could be fortunately separated in the later stage.

Namely, prior to the present invention, there is no efficient method for producing optically active cyclohexenone derivatives.

Considering the above, the inventors of the present invention have earnestly studied to attain the object and to efficiently obtain optically active cyclohexenone derivatives having high purity as intermediates for synthesizing natural compounds, so that they have found optically active cyclohexene derivatives useful as intermediates and the optically active cyclohexenone derivatives, and the method for producing efficiently the compounds has been established.

SUMMARY OF THE INVENTION

In the present invention, an optically active cyclohexenone derivative is obtained by the process comprising using as a starting material cyclohexene diol represented by the formula:

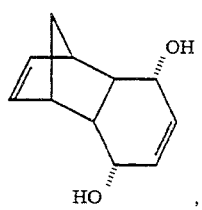

(6)

reacting the cyclohexene diol with an ester in the presence of lipase by transesterification selectively in positions to obtain an optically active cyclohexene derivative represented by the general formula:

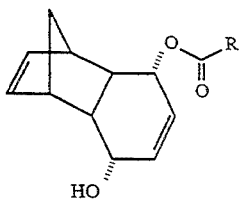

(1)

or

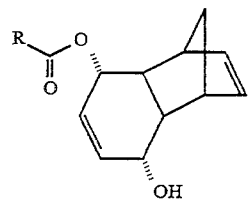

(1')

wherein R is alkyl, then oxidizing the hydroxy group of the derivative to obtain an optically active cyclohexenone derivative represented by the formula:

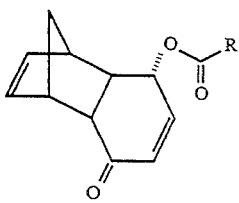

(2)

or

-continued

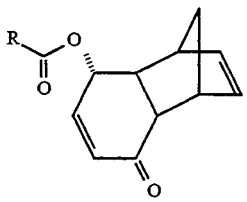
(2')

wherein R is alkyl, and reacting the resultant derivative by deacyloxylation to obtain an optically active cyclohexenone derivative represented by the formula:

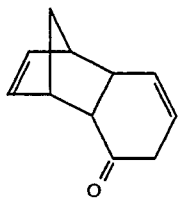
(3)

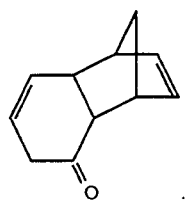
(3')

The alkyl group R is preferably a $C_1$ to $C_{35}$ alkyl. Then, the last compound is isomerized to obtain an optically active cyclohexenone derivative represented by the formula:

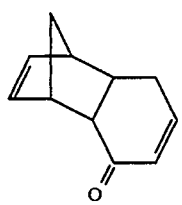
(4)

or

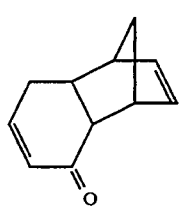
(4')

reacting the resultant compound with a grignard reagent to obtain an optically active derivative represented by the formula:

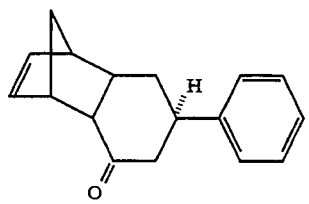
(5)

or

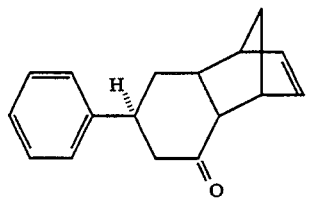
(5')

and reacting the resultant compound by a retro Diels-Alder reaction to obtain an optically active cyclohexenone derivative represented by the formula:

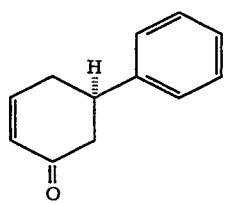
(7)

or

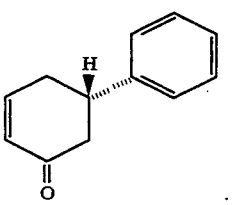
(7')

The reaction steps of the process of the present invention are exemplified in the following:

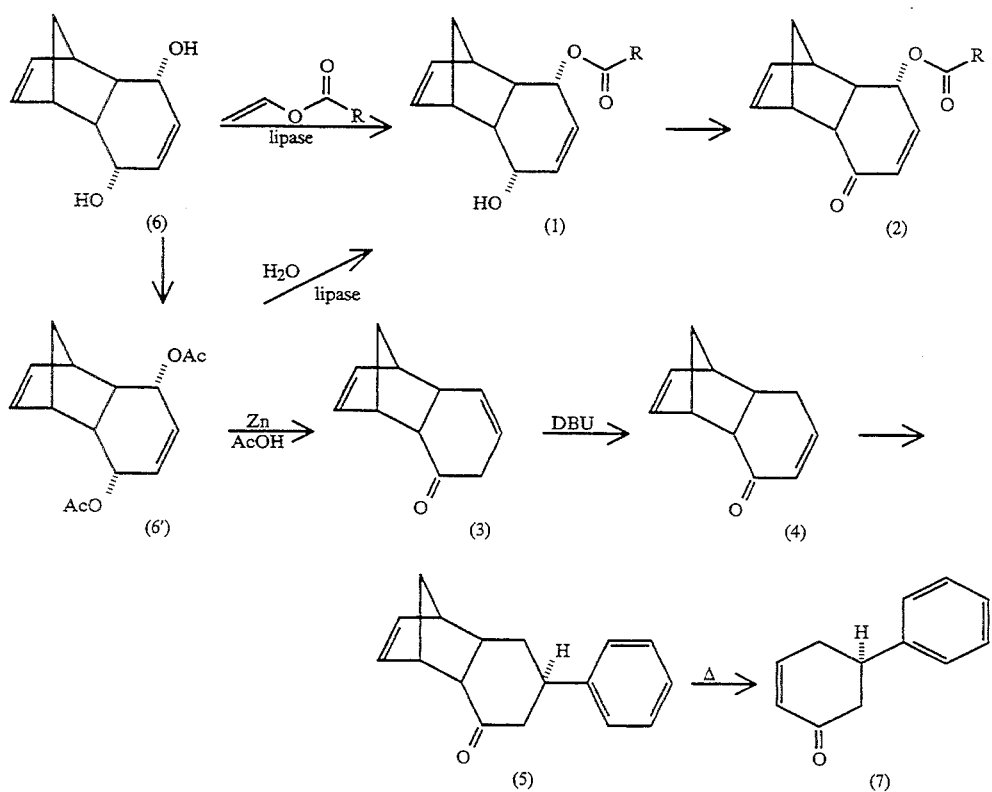

The hexene diol derivative (6) of the starting material in the present invention is easily obtained by reduction of a carbonyl group of a cyclohexenone derivative, which is obtained by a common Diels-Alder reaction of cyclopentadiene and hydroquinone, in the presence of a reducing agent such as lithium aluminum hydride.

The resultant hexenediol derivative (6) is reacted by transesterification with a specified ester in the presence of lipase. Otherwise, the derivative (6) is reacted by a conventional method and the obtained diacetate is hydrolyzed in the presence of lipase. Then, the optically active cyclohexene derivative (1) or (1') of the present invention can be obtained. In the case of the transesterification reaction, fatty acid vinyl esters, triglycerides, acid anhydrides and several kinds of esters are exemplified as the specified esters, and fatty acid vinyl esters are preferably used. Any lipase having catalytic effect in the reaction can be used, and particularly, commercially available lipase PS (manufactured by Amano Pharmaceutical Co., Ltd.) derived from a Pseudomonus genus is preferred. Any solvent by which the reaction is not inhibited can be used, or the reaction can be conducted in the presence of the substrate alone and without solvent. Preferably, acetonitrile can be used as a reaction solvent.

In the case of the hydrolysis reaction, the optically active cyclohexene derivative (1) or (1') may be obtained by the process comprising adding the diacetate of cyclohexenediol (6') into a lipase suspended buffer solution of phosphoric acid (preferably, buffer-/acetone=9/1(V/V)), and hydrolyzing the mixture. The pH value of the phosphoric acid buffer depends on the lipase, and it is 4–9, preferably 7–8. As the lipase, if it acts as a catalyst of stereoselective hydrolysis reaction, any kinds of lipase may be used. As microorganisms, the genera Pseudomonas, Arthrobacter, Alcaligenes, Aspergillus, Chromobacterium, Candida, Mucor, Rhizopus, etc. can be exemplified. The lipase may be extracted from the viscera animals, for example, the liver or the pancreas of pig or cattle. Particularly lipase from a Pseudomonas genus can be preferably used. As commercially available lipase, lipase PS, OF, AY and AK (manufactured by Amano Pharmaceutical Co., Ltd.), MY (manufactured by The Meito Sangyo Co., Ltd.) and PPL (manufactured by Sigma Co.) can be exemplified, and PS is desirable. To immobilize the lipase, as carriers immobilizing the lipase, Chromosorb, Celite, cellulose, carrageenan or various synthetic polymers by which the lipase activity is not inhibited can be used.

When the cyclohexene derivative (1) is reacted with an oxidizing agent such as manganese dioxide by common oxidation reaction, a hydroxyl group is changed into a carbonyl group to obtain the cyclohexene derivative represented by the formula (2).

Then the resultant derivative is treated with ultrasonic waves in the presence of zinc to deacyloxylate by a common method, and the cyclohexenone derivative represented by the formula (3) can be obtained.

Further, the resultant compound is isomerized by a common method to obtain the cyclohexenone derivative represented by the formula (4).

The compound (4) is reacted with a Grignard reagent such as phenyl magnesium bromide by a nucleophilic reaction (Takei et al., Tetrahedron Lett., 28, 5669 (1987)), and the cyclohexanone derivative represented by the formula (5) is obtained.

The compound can be changed into the optically active cyclohexenone derivative represented by the formula (7) useful as an intermediate of natural compounds by a general retro Diels-Alder reaction.

The present invention provides the following merits.

1. Optically active cyclohexene derivatives useful for natural material synthesis, which are represented by the above formulas (1) or (1')–(4) or (4') and (7) or (7'), are obtained efficiently and the derivatives have high purity.
2. Each intermediate represented by the above formulas (1) or (1')–(5) or (5') and (7) or (7') can be changed into useful chiral elements.
3. The cyclohexene derivative represented by the above formula (1) or (1') is a meso compound, so that it acts as two antipodes by distinction between a hydroxy group and an acyloxy group. Accordingly, the compound (1) or (1') can be prepared from the same compound (6), and the compound (2) or (2') and the like can be prepared similarly.

DESCRIPTION OF PREFERRED EMBODIMENTS

The following examples illustrate this invention more specifically, but these will not always be precise in practical applications.

Example 1

To an acetonitrile solution of a hexenediol derivative (6) (100 mg, 0.56 mmol) and vinyl acetate (0.3 ml, 3.36 mmol) lipase PS (100 mg) was suspended, and the mixture was stirred for two weeks at room temperature. After the lipase was filtered away, the filtrate was concentrated under reduced pressure, and the residue was purified with a chromatograph over silica gel to obtain a diacetate (5 mg, 3.4%), a monoacetate (1) (101 mg, 89%) and 15 mg of unreacted materials. The specific rotation of the monoacetate was $[\alpha]_D^{29}$ 63.1° (c2.20, CHCl$_3$). Further, the other values of physical properties were as follows:

IR (neat) 1737 cm$^{-1}$
$^1$H-NMR (90 MHz), CDCl$_3$
1.20–1.40(m, 2H), 1.73–2.25(br, 1H), 2.08(s, 3H), 2.71–3.18(m, 4H), 4.39–4.48(m, 1H), 5.19–5.57(m, 3H), 5.74–5.93(m, 2H).

Example 2

A dichloromethane solution (5 ml) of the monoacetate (1) (600.3 mg, 2.72 mmol) was added dropwise in a suspended dichloromethane solution (10 ml) of manganese dioxide (3.56 g, 40.9 mmol) on ice cooling, and the mixture was stirred for 30 minutes at the same temperature. Unreacted materials were filtered off, the filtrate was concentrated under reduced pressure, and the residue was chromatographed over silica gel to obtain a ketone (2) (491 mg, 82%). The specific rotation was $[\alpha]_D^{29}$ −219.9° (c1.29, CHCl$_3$). Further, the value of elemental analysis was as follows:

Calculated C:71.54, H:6.47
Found C:71.43, H:6.47

The other values of physical properties were as follows:

IR (neat) 1741, 1669 cm$^{-1}$
$^1$H-NMR (90 MHz), CDCl$_3$
1.23–1.51(m, 2H), 2.17(s, 3H), 2.89–3.48(m, 4H), 5.60–5.93(m, 3H), 6.11(dd, 1H, J=5.4 Hz, 2.7 Hz), 6.45(ddd, 1H, J=10.2, 2.4, 1.0 Hz)

Example 3

To a mixed solution of the ketone (2) (97 mg, 0.44 mmol) in ethanol-acetic acid (2.1 ml–0.7 ml), 150 mg of Zinc powder was suspended, and the mixture was irradiated with ultrasonic wave at room temperature for 3.5 hours. Insoluble materials were filtered off, the filtrate was concentrated under reduced pressure, and the residue was extracted with ether. The ether layer was washed with 5% aqueous solution of sodium bicarbonate and with water, and then the layer was dried over magnesium sulfate. The solvent was distilled away under reduced pressure, and the residue was chromatographed over silica gel to obtain the compound represented by the formula (3) (42 mg, 43%). The values of physical properties were as follows:

IR (neat) 1701 cm$^{-1}$
$^1$H-NMR (90 MHz), CDCl$_3$
1.31–1.55(m, 2H), 2.31–2.74(m, 2H), 2.80–3.22(m, 3H), 2.80–3.22(m, 3H), 3.28–3.46(m, 1H), 5.43–5.64(m, 1H), 5.72–5.89(m, 1H), 5.98–6.28(m, 2H)

Example 4

A $\beta$,$\gamma$-unsaturated ketone (3) (42 mg, 0.26 mmol) and DBU (0.04 ml, 0.26 mmol) were dissolved in benzene (2 ml), and the mixture was stirred overnight at room temperature. Benzene was distilled away under reduced pressure, the residue was chromatographed over silica gel, and a $\alpha$,$\beta$-unsaturated ketone (4) (10 mg, 24%) was obtained. The values of physical properties were as follows:

IR (neat) 1662 cm$^{-1}$
$^1$H-NMR (90 MHz), CDCl$_3$
1.24–1.52(m, 2H), 1.84–2.26(m, 1H), 2.39–3.10(m, 4H), 3.30–3.48(m, 1H), 5.78–5.97(m, 1H), 6.04–6.23(m, 2H), 6.57–6.79(m, 1H)

Example 5

A $\alpha$,$\beta$-unsaturated ketone (4) (10 mg, 24%) was dissolved in 10 ml of THF. To the solution, phenyl magnesium bromide (0.075 mmol, 10 ml of a THF solution) previously prepared was added dropwise on ice cooling. After stirring for four hours, the reaction mixture was injected into a saturated solution of ammonium chloride on ice cooling. After the mixture was extracted with ether, the ether layer was washed with saturated sodium chloride solution. The ether layer was dried over magnesium sulfate, then ether was distilled away under reduced pressure, and the residue was obtained. The residue was purified by silica gel chromatography to obtain an optically active cyclohexanone derivative (5) (9 mg, 62%). Further, the compound in 1 ml of a diphenyl ether solution was heated and refluxed for 1.5 hours. The mixture solution was chromatographed over silica gel to obtain an optically active cyclohexenone derivative represented by the formula (6) (2.5 mg, 90%). The specific rotation was $[\alpha]_D^{31}$ −47.9° (c0.52, CHCl$_3$), (a literature value; $[\alpha]_D^{23}$ −46.4° (c5.0, CHCl$_3$), and the result fits in with the literature value.

Example 6 Synthesis of eutypoxide B (Application example)

Step 1

Vinyl magnesium bromide (2.1 ml, 1M THF sol.) was added to 4 ml of a THF solution of copper (I) bromide-dimethyl sulfide complex (7 mg, 0.03 mmol) and HMPA (0.25 ml, 1.4 mmol) at −78° C. and the mixture was stirred for 10 minutes. A mixture of the enone (153 mg, 0.70 mmol) obtained by Example 5 and trimethylsilyl chloride (0.36 ml, 2.84 mmol) dissolved in 2 ml of THF was added dropwise to the above mixture and stirred for one hour at −78° C. Then, 3 ml of 5% hydrochloric acid was added. After rising to room temperature the mixture was stirred for 30 minutes. The reaction solution was diluted with ether, and washed with water, with saturated sodium bicarbonate solution and then with saturated sodium chloride solution. The ether layer was dried over magnesium sulfate, then ether was distilled away under reduced pressure, and the residue was obtained. The residue was purified by silica gel chromatography to obtain a ketone (140 mg, 81%) of colorless crystals.

m.p. 73°–74° C.
$[\alpha]_D^{32}$ +20.9° (c0.94, CHCl$_3$)
IR (nujol) 1723, 1687 cm$^{-1}$
$^1$H-NMR (300 MHz), CDCl$_3$; 1.29(br. d, J=8.4 Hz, 1H), 1.41(br. d, J=8.6 Hz, 1H), 2.11(s, 3H), 2.11–2.33(m, 2H), 2.53–2.61(m, 1H), 2.90–2.96(m, 2H), 3.05–3.12(m, 1H), 3.38(br. s, 1H), 4.98–5.07(m, 2H), 5.18(dd, J=10.7, 8.1 Hz, 1H), 5.60(ddd, J=17.2, 10.6, 6.3 Hz, 1H), 6.14–6.21(m, 2H)
MS m/e 246(M$^+$), 66(100%)
HRMS calcd for C$_{15}$H$_{18}$O$_3$ 246.1256, Found 246.1253
Anal. calcd for C$_{15}$H$_{18}$O$_3$: C73.15; H 7.37 Found C 73.14; H 7.34.

Step 2

Sodium borohydride (94 mg, 2.5 mmol) was added to 3 ml of a methanol solution of the ketone (305 mg, 1.24 mmol) obtained by Step 1 on ice cooling, and the mixture was stirred at the same temperature for 30 minutes. After rising to room temperature, potassium carbonate (300 mg, 2.17 mmol) was added, and the mixture was stirred for 12 hours. The mixture was diluted with dichloromethane and washed with saturated sodium chloride solution. The dichloromethane layer was dried over magnesium sulfate, then the organic solvent was distilled away under reduced pressure, and the residue was chromatographed over silica gel to obtain a diol (235 mg, 92%).

m.p. 132°–133° C.
$[\alpha]_D^{27}$ +72.2° (c1.16, MeOH)
IR (nujol) 3235 cm$^{-1}$
$^1$H-NMR (300 MHz), CDCl$_3$; 1.33(d, J=8.1 Hz, 1H), 1.45–1.54(m, 2H), 1.85(ddd, J=14.7, 10.2, 7.3 Hz, 1H), 2.01(br. d. J=5.1 Hz, 1H), 2.30–2.36(m, 1H), 2.45–2.54(m, 2H), 2.62(ddd, J=11.0, 5.1, 3.3 Hz, 1H), 2.94–2.98(m, 1H), 3.76–3.82(m, 1H), 4.14–4.18(m, 1H), 5.00–5.06(m, 2H), 5.71(ddd, J=16.9, 9.9, 8.4 Hz, 1H), 6.18–6.25(m, 2H)
MS m/e 206(M$^+$), 66(100%)
HRMS calcd for C$_{13}$H$_{18}$O$_2$ 206.1307, Found 206.1313
Anal. calcd for C$_{13}$H$_{18}$O$_2$: C 75.69; H 8.8; Found C 75.69; H 8.8.

Step 3

Four ml of a diphenyl ether solution of the diol (100 mg, 0.49 mmol) obtained by Step 2 was refluxed for 45 minutes. The reaction solution was chromatographed over silica gel to obtain a retro D-A product (50 mg, 73%).

$[\alpha]_D^{30}$ −33.2° (c0.43, MeOH)
IR (film) 3328 cm$^{-1}$
$^1$H-NMR (300 MHz), CDCl$_3$; 1.57(ddd, J=14.3, 12.1, 4.4 Hz, 1H), 1.72(dt, J=13.5, 3.0 Hz, 1H), 2.26–2.37(m, 1H), 3.71(d, J=8.5 Hz, 1H), 4.01–4.04(m, 1H), 4.93–5.08(m, 2H), 5.69(br. s, 2H), 5.79(ddd, J=14.5, 10.6, 7.3 Hz, 1H)
MS m/e 122(M$^+$−18), 86(100%)
HRMS calcd for C$_8$H$_{10}$O 122.0732, Found 122.0725

Step 4

Imidazole (50 mg, 0.73 mmol) and t-butyldimethylsilyl chloride (81 mg, 0.54 mmol) were added to 0.5 ml of a DMF solution of retro D-A product (25 mg, 0.18 mmol) on ice cooling, and the mixture was stirred for four hours at room temperature. Ether was added to the reaction solution, and the solution was washed with saturated sodium chloride and dried over magnesium sulfate. The solvent was distilled away under reduced pressure, and the residue was chromatographed over silica gel to obtain t-butyldimethylsilyl ether (62 mg, 94%).

$[\alpha]_D^{26}$ −9.6° (c1.03, CHCl$_3$)
IR (film) 1642 cm$^{-1}$
$^1$H-NMR (90 MHz), CDCl$_3$; 0.06(s, 12H), 0.90(s, 18H), 1.42–1.91(m, 2H), 2.34–2.58(m, 1H), 3.86(d, J=8.0 Hz, 1H), 4.10–4.22(m, 1H), 4.95–5.19(m, 2H), 5.65(d, J=1.2 Hz, 2H), 5.65–6.12(m, 1H)
MS m/e 368(M$^+$), 147(100%)
HRMS calcd for C$_{16}$H$_{34}$O$_2$Si$_2$ 314.2097 (M$^+$−54), Found 314.2110

Step 5 m-Chloroperbenzoic acid (205 mg, 0.83 mmol) and 4,4′-Thiobis (6-tert-butyl-m-cresol) (10 mg, 0.028 mmol) were added to 5 ml of a dichloroethane solution of t-butyldimethylsilyl ether (102 mg, 0.28 mmol), and the mixture was refluxed for 5 minutes. The mixture was diluted with dichloromethane, and washed with saturated sodium bicarbonate solution and then with saturated sodium chloride solution. The organic layer was dried over magnesium sulfate, and the solvent was distilled away under reduced pressure. The residue was chromatographed over silica gel to obtain a diepoxide (82 mg, 74%).

$^1$H-NMR (90 MHz), CDCl$_3$; 0.10(s, 8H), 0.17(s, 4H), 0.90, 0.93, 0.94(3s, 18H), 1.15–1.68(m, 3H), 2.35–2.79(m, 3H), 3.07(br. s, 2H) 3.73(d, J=8.6 Hz, 1H), 4.18–4.29(m, 1H)
MS m/e 343(M$^+$−$^t$Bu), 147(100%)
HRMS calcd for C$_{16}$H$_{31}$O$_2$Si$_2$ 343.1761(M$^+$−$^t$Bu), Found 343.1754

Step 6

Isopropenylmagnesium bromide (2 ml, 0.6M-THF sol., 1.2 mmol) was added to 2 ml of a THF solution of diepoxide (82 mg, 0.21 mmol) and CuI (5 mg, 0.03 mmol) at −20° C., and the mixture was stirred at −15° C. for 4 hours. A saturated solution of ammonium chloride was added to the reaction solution, and the solution was extracted with ether. The ether layer was washed with water, with saturated sodium bicarbonate solution and with saturated sodium chloride solution. The ether layer was dried over magnesium sulfate. The solvent was distilled away under reduced pressure and a crude product (111 mg) was obtained. The product was dissolved in 3 ml of dichloromethane, pyridinium chlorochromate (90 mg, 0.41 mmol) was added, and the mixture was stirred for 10 hours at room temperature. 3 g of silica gel was added to the reaction solution, and the solution was filtered with cerite. The solvent was distilled away from the filtrate and the residue was chromatographed over silica gel to obtain a ketone (60 mg, 89%).

m.p. 78°–79° C.
$[\alpha]_D^{29}$ +18.3° (c0.71, CHCl$_3$)
IR (nujol) 1706 cm$^{-1}$
$^1$H-NMR (300 MHz), CDCl$_3$; 0.04(s, 3H), 0.11(s, 3H), 0.12 (s, 3H), 0.14(s, 3H), 0.89(s, 9H), 0.94(s, 9H), 1.45–1.56(m, 2H), 1.74(s, 3H), 2.98(t. d, J=9.5, 5.4 Hz, 1H), 3.04–3.08(m, 2H), 3.09(d, J=15.0 Hz, 1H), 3.17(d, J=15.0 Hz, 1H), 4.12(d, J=9.5 Hz, 1H), 4.21–4.25(m, 1H), 4.81(s, 1H), 4.94(s, 1H),
MS m/e 425(M$^+$−CH$_3$), 73(100%)

HRMS calcd for C$_{22}$H$_{41}$O$_4$Si$_2$ 425.2543(M$^+$ — CH$_3$), Found 425.2549

Anal. calcd for C$_{22}$H$_{41}$O$_4$Si$_2$: C 62.68; H 10.06; Found C 62.82; H 10.06.

Step 7

Bu$_4$NF (0.20 ml, 1M-THF sol. 0.2 mmol) was added to the enome (20 mg, 0.045 mmol) obtained by Step 6, and the mixture was stirred for one hour. After saturated sodium chloride solution was added, the mixture was extracted with ethyl acetate, and the organic layer was dried over magnesium sulfate. The solvent was distilled away under reduced pressure, and the residue was chromatographed over silica gel to obtain eutypoxide B (6.1 mg, 63%).

$[\alpha]_D^{23}$ —56.6° (c0.68, CHCl$_3$)

IR (film) 3414, 1678, 1614 cm$^{-1}$ $^1$H-NMR (300 MHz), CDCl$_3$; 1.50(t. d, J=13.9, 2.9 Hz, 1H), 1.80(t. d, 12.1 Hz, 2.8 Hz, 1H), 1.92(d, J=1.1 Hz, 2.06(d, J=5.5 Hz, 1H), 2.16(d, J=0.7 Hz, 3H), 2.67(ddd, 12.8, 9.5, 2.5 Hz, 1H), 2.89(d, J=4.4 Hz, 1H), 3.22(br. s, 1H), 3.25(d, J=3.3 Hz, 1H), 4.25(dd, J=4.4, 9.5 Hz, 1H), 4.36–4.42(m, 1H), 6.14(br. s, 1H)

MS m/e 212(M$^+$), 83(100%)

HRMS calcd for C$_{11}$H$_{16}$O$_4$ 212.1049(M$^+$), Found 212.1000

Example 7

To 30 ml of a phosphoric acid buffer containing 10% (v/v) acetone, 3,6-diacetyloxytricyclo [6,2,1,0$^{2.7}$] undeca-4,9-diene (8) (1.31 g, 5.0 mmol) was mixed. After lipase PS (30 mg) was added, and the mixture was shaken at 27° C. After 24 hours, the reaction solution was filtered with cerite, the filtrate was extracted with ether. The organic layer was dried over magnesium sulfate, and the solvent was distilled away under reduced pressure. The residue was purified with a chromatograph over silica gel to obtain a monoacetate (1') (930 mg, 4.23 mmol, 85%). The specific rotation of the monoacetate was $[\alpha]_D^{29}$ —62.8° (c2.0, CHCl$_3$). Further, the data of $^1$H-NMR fit in with those of the compound (1) of Example 1.

We claim:

1. An optically active cyclohexene derivative represented by the general formula:

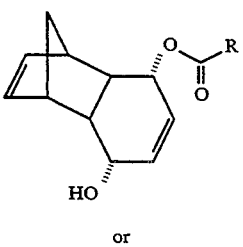
(1)

or

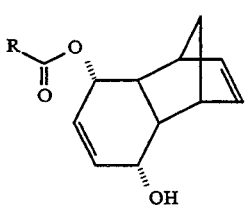
(1')

wherein R is alkyl.

2. An optically active cyclohexenone derivative represented by the general formula:

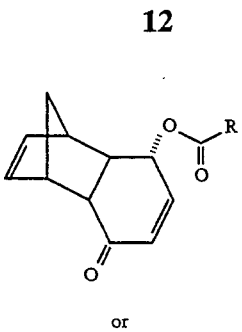
(2)

or

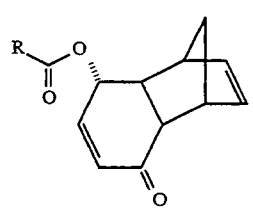
(2')

wherein R is alkyl.

3. An optically active cyclohexenone derivative represented by the following formula:

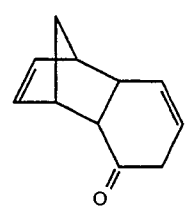
(3)

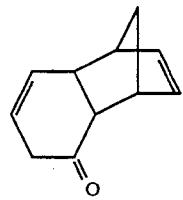
(3')

4. An optically active cyclohexenone derivative represented by the formula:

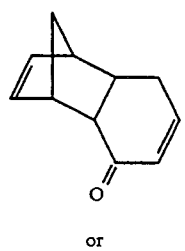
(4)

or

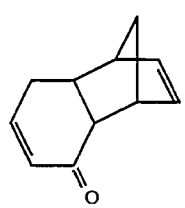
(4')

5. An optically active cyclohexanone derivative represented by the following formula:

(5)

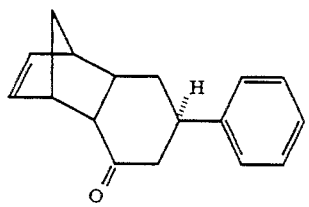

or (5')

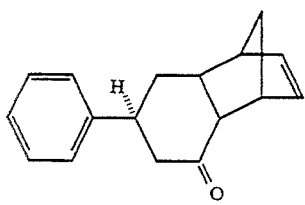

6. A process for producing an optically active cyclohexene derivative comprising using cyclohexene diol as a starting material represented by the following formula:

(6)

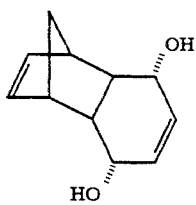

and reacting the cyclohexene diol with a specified ester in the presence of lipase by transesterification selectively in positions to obtain the optically active cyclohexene derivative represented by the formula (1) or (1') described in claim 1.

7. A process for producing an optically active cyclohexenone derivative comprising using an optically active cyclohexenone derivative represented by the formula (2) or (2') described in claim 2 as a starting material, by way of an optically active cyclohexenone derivative represented by the formula (3) or (3'), an optically active cyclohexenone derivative represented by the formula (4) or (4') and an optically active cyclohexanone derivative represented by the formula (5) or (5'), and obtaining the optically active cyclohexenone derivative represented by the following formula:

(7)

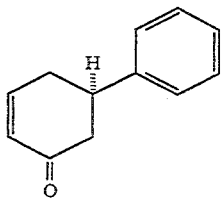

or (7')

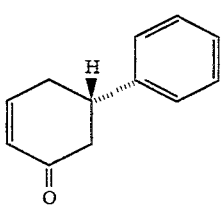

8. A process for producing an optically active cyclohexene derivative comprising using diacyloxy cyclohexene derivative as a starting material represented by the following formula:

(8)

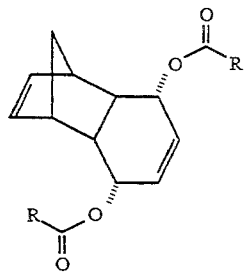

and reacting the diacyloxy cyclohexene derivative in the presence of lipase by stereoselective hydrolysis to obtain the optically active cyclohexene derivative represented by the formula (1) or (1') described in claim 1.

* * * * *